United States Patent
Conner

(10) Patent No.: US 7,296,475 B2
(45) Date of Patent: Nov. 20, 2007

(54) DISPLACEMENT INSTRUMENT FOR DETERMINING THE MODULUS OF A MATERIAL

(76) Inventor: Charles C. Conner, P.O. Box 355, Hemet, CA (US) 92546

( * ) Notice: Subject to any disclaimer, the term of this patent is extended or adjusted under 35 U.S.C. 154(b) by 0 days.

(21) Appl. No.: 11/378,526

(22) Filed: Mar. 18, 2006

(65) Prior Publication Data

US 2006/0219001 A1 Oct. 5, 2006

(51) Int. Cl.
*G01L 7/16* (2006.01)
*G01D 11/24* (2006.01)
*G01B 5/30* (2006.01)

(52) U.S. Cl. .............................. 73/754; 73/431; 73/763; 73/784; 173/4; 173/11; 173/20; 702/42; 702/43

(58) Field of Classification Search .......... 73/700–756, 73/784, 781, 431; 173/3, 4, 11, 20; 702/42, 702/43
See application file for complete search history.

(56) References Cited

U.S. PATENT DOCUMENTS

| | | | | |
|---|---|---|---|---|
| 2,995,721 A | * | 8/1961 | Di Giovanni ................... 338/4 |
| 3,195,354 A | * | 7/1965 | Douslin ...................... 73/64.45 |
| 4,219,776 A | * | 8/1980 | Arulanandan ................ 324/323 |
| 4,315,429 A | * | 2/1982 | Morozov et al. .............. 73/84 |
| 4,347,743 A | * | 9/1982 | Rausche et al. .............. 73/654 |
| 4,586,366 A | * | 5/1986 | Milberger ................... 73/11.03 |
| 5,168,938 A | * | 12/1992 | Sano et al. ..................... 173/11 |
| 5,249,892 A | * | 10/1993 | Fox et al. .................... 405/233 |
| 5,978,749 A | * | 11/1999 | Likins et al. ................ 702/158 |
| 6,431,006 B1 | * | 8/2002 | Henke et al. .................. 73/784 |
| 6,533,502 B2 | * | 3/2003 | McVay et al. ............... 405/232 |
| 6,604,432 B1 | * | 8/2003 | Hamblen et al. ............. 73/784 |
| 7,073,374 B2 | * | 7/2006 | Berkman ........................ 73/78 |
| 7,107,159 B2 | * | 9/2006 | German ........................ 702/41 |
| 2004/0035207 A1 | * | 2/2004 | Hamblen et al. ............. 73/573 |
| 2005/0199045 A1 | * | 9/2005 | Briaud et al. .................. 73/84 |

* cited by examiner

*Primary Examiner*—Hezron Williams
*Assistant Examiner*—David A. Rogers
(74) *Attorney, Agent, or Firm*—Klarquist Sparkman, LLP

(57) ABSTRACT

A novel displacement instrument that can be used to measure the density or modulus of an aggregate pier upon which a multistory building or parking garage can be built. The aggregate piers are often 35 feet or deeper. These aggravate piers are constructed by adding lifts of approximately 12 to 18 inches of aggregate at a time and tamping it into the pier forming hole. Each lift of aggregate is being tamped or struck by a force of approximately 15,000 psi or greater. The displacement instrument allows aggregate piers to be constructed having a density or modulus that is consistent from the bottom of the hole to the top of the hole. The displacement instrument would be mounted on the side plate of a hydraulic breaker that is mounted on the end of a boom of a crane. The displacement instrument need not be permanently installed on the side of the hydraulic breaker and it is freely removed and installed on another crane.

8 Claims, 6 Drawing Sheets

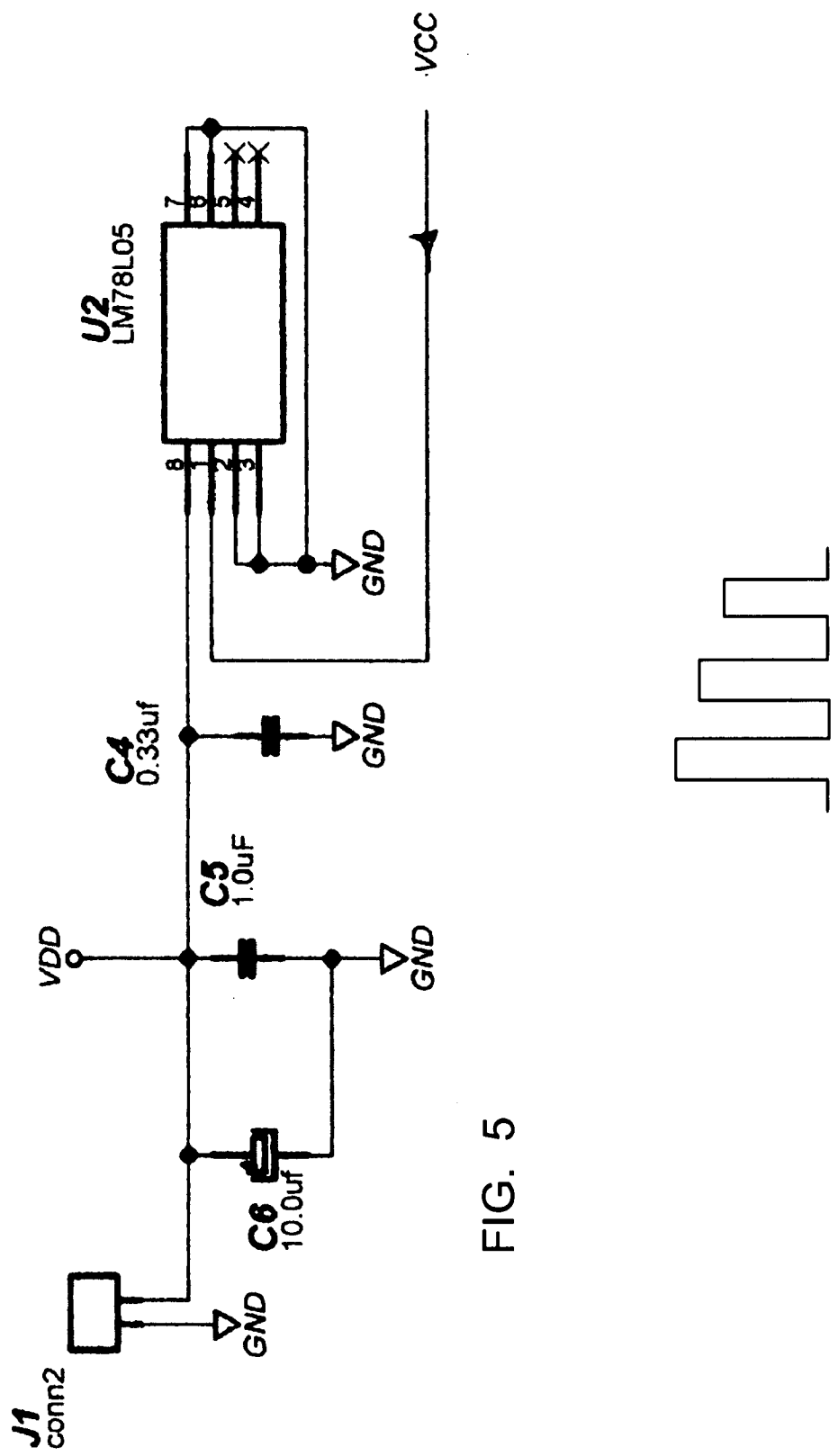

DISPLACEMENT INSTRUMENT FOR DETERMINING THE MODULUS OF A MATERIAL

BACKGROUND OF THE INVENTION

The invention relates to a measuring instrument and more specifically to an instrument for measuring the density or modulus of material that has been subjected to compression forces.

All earth materials possess specific discrete strength and compression characteristics that must be defined in order to design structures to be supported on those materials. These various characteristics are referred to as the soil's "Engineering Properties." One of these properties is the soil "modulus," which relates deformation of the soil to an applied load that causes the deformation. Modulus is a very significant engineering property for designing floor slabs on-grade and footings, and for estimating settlements.

Engineering properties of soils can be determined by means of special field and/or laboratory tests. Laboratory tests are often of questionable value due to the inability of the engineer to obtain a truly "undisturbed" sample of the soil for the test. Additionally, most field tests for engineering properties (including modulus:) are labor intensive and require significant time to conduct. Nonetheless designs for pavements, slabs on-grade, and foundations using subgrade modulus were developed and widely used in the $19^{th}$ and $20^{th}$ centuries by the Civil Aeronautical Administration (CCA, now known as the Federal Aviation Administration) and the U.S. Navy.

Since engineering properties tests are typically relatively slow and costly, a number of faster and less costly "Index Tests" have been developed over the years which enable the designer to estimate the engineering properties he needs based on correlations with various index test results. Typical index tests include moisture content, density, various penetration tests, and others. Due to the variations in soils in nature, and inherent difficulties in correlating index test results to soil type, the estimation of a modulus value for a given soil based on index tests can result in a crude approximation at best. Hence, designs based either primarily or solely on estimating modulus from index tests must include relatively large factors of safety in order to, hopefully, account for errors in the correlations.

With the advent of the nuclear densometer (a rapid, in-place density testing device), the practice of evaluating subgrade modulus in the field by direct measurement (i.e., by means of a time consuming plate load test) was replaced almost exclusively by correlation with in-place density. Additional developments in field penetration testing (the Cone Penetration Test and standard Penetration Test), which are also index tests, further reduced the determination of soil modulus by direct measurement in the field. In response, other field tests have been developed to measure soil modulus in the field (i.e., pressure meter and dilatometer); however, these tests employ a horizontal force applied to the soil within a borehole, and the modulus corresponding to a vertically applied force is inferred by means of soil mechanics principles. Since the design of pavements, slabs on-grade and foundations rely on the soil modulus resulting from a vertically applied load, these more recent field tests still provide only an indication of the appropriate modulus for design. Further, the pressure meter and dilatometer tests are time consuming and costly.

Now, as a result of the development of this displacement instrument it is possible to directly, accurately and economically measure the soil modulus in-place, and in the vertical direction. By so doing, design and construction cost savings could be realized by further minimizing necessary soil testing and by potentially reducing the factors of safety applied in conventional engineering design. Specific applications could include establishing design modulus values in the field during soils investigations, confirming selected design modulus values during preconstruction site grading and confirming the modulus improvement achieved by various sub-grade stabilization/reenforcement techniques.

It is an object of the invention to provide a novel displacement instrument that overcomes an existing problem of not being able to measure the modulus or density of the aggregate piers produced by the method disclosed in U.S. Pat. No. 6,453,766.

It is another object of the invention to provide a novel displacement instrument that allows each of the lifts of approximately 12-18 inches of aggregate that is tamped into a pier forming hole to be tested at that time for its density or modulus. These pier holes are often up to 35 feet deep or deeper.

It is also an object of the invention to provide a novel displacement instrument that will allow aggregate piers to be constructed having a density or modulus that is consistent from the bottom of the hole to its top.

It is an additional object of the invention to provide a novel displacement instrument that can be mounted on the side of a hydraulic breaker mounted on the front end of the boom of a crane.

It is a further object of the invention to provide a novel displacement instrument that can withstand the constant repetitive strokes of the tamper plate striking the aggregate at a force of 15,000 psi or greater.

It is another object of the invention to provide a novel displacement instrument that is portable so that it can be removed from any hydraulic breaker when not in use or installed on another hydraulic breaker.

It is also an object of the invention to provide a novel displacement instrument having a free floating circuit board with an air pressure transducer mounted thereon.

SUMMARY OF THE INVENTION

For decades the foundation for structures consisted of digging a hole in the soil, filling the hole with cement and/or driving piling. A preferred method has been developed whereby a hole is dug in the soil and filled with layers of aggregate, each layer compacted to a desired modulus (density) as the pier is built. This method has proven to be more reliable and less costly than the cement pile process (See U.S. Pat. Nos. 5,249,892 and 6,345,766).

One weakness in the aggregate pier method is the lack of modulus consistency in each layer of aggregate within the pier and the modulus consistency of each pier within the entire construction site. This inconsistency in the pier modulus results in excessive over design with all of the undesirable effects that over design creates.

The instrument described herein measures the aggregate modulus layer by layer as the pier is built. The instrument will measure displacements along a prescribed axis on any vector, individually and/or collectively. The instrument transforms these displacements into electric signals suitable for processing. Processing and/or calibrating these signals provides an avenue to measure a variety of functions dynamically, including but not limited to, modulus, density, penetration, etc.

When loose aggregate is confined in a container with a controlled applied force, the modulus (density) may be determined by measuring the displacement of the tool used to apply the force. In the case of a foundation the axis of the applied force delivered by an appropriate tool to the aggregate is vertical therefore the measurement of the vertical displacement of the tool is directly related to the modulus of the aggregate. This procedure maintains a uniform modulus throughout the pier and throughout all of the piers of the project. This method will eliminate the approximation procedures of the present construction process.

DESCRIPTION OF THE DRAWINGS

FIG. 5 shows the electrical circuitry on the printed circuit board for the voltage regulator that is connected to the pressure transducer;

FIG. 6 is a voltage output signal from the displacement instrument;

DESCRIPTION OF THE PREFERRED EMBODIMENT

The novel displacement instrument will now be described by referring to FIGS. 1-8 of the drawings. The displacement instrument is generally designated numeral 10.

Figure 1:
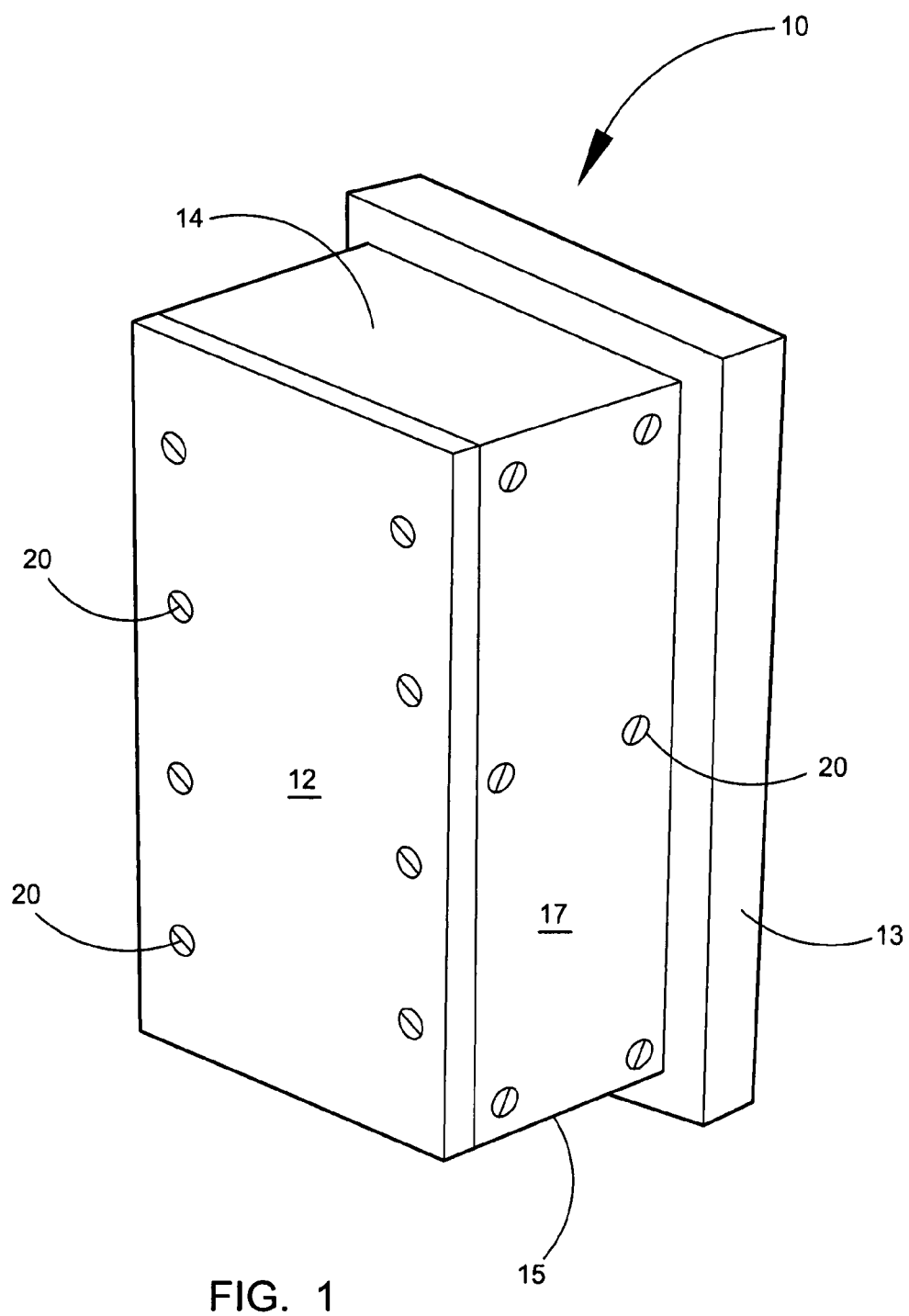
FIG. 1 is a front perspective view of the novel displacement instrument.

FIG. 1 shows the displacement instrument 10 having a housing or casing formed from a front cover plate wall 12, a rear plate wall 13, a top plate wall 14, a bottom plate wall 15, a left side plate wall 16 and a right side plate 17. The respective plates have a thickness in the order of ⅜ inch although they could be either thicker or thinner. The plates would normally be made from aluminum or a steel alloy, although other materials could be used. The respective plate members are connected to each other by bolts 20. The housing casing illustrated has an approximate width of 4 inches, an approximate depth of 4 inches and a height of approximately 10 inches. These dimensions are not critical and larger or smaller dimensions might be used in different applications.

Figure 2:
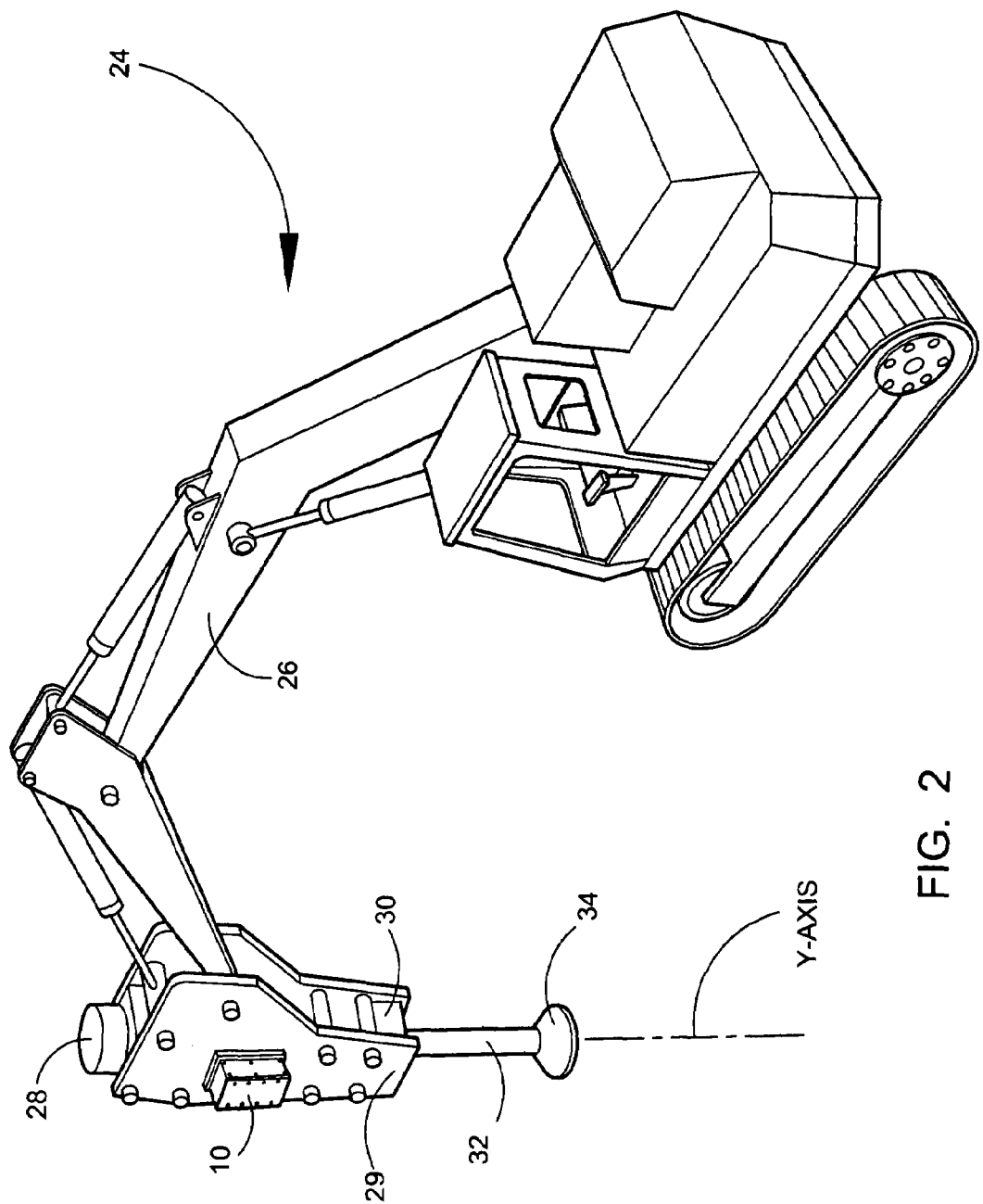
FIG. 2 shows the displacement instrument mounted on the hydraulic breaker assembly of a crane.

A crane 24 is illustrated in FIG. 2 having an articulated boom 26 having a hydraulic system that powers hydraulic breaker 28. Hydraulic breaker 28 has side plates 29 and 30 and displacement instrument 10 would be fastened to side plate 29 by removable bolts. A shaft 32 extends downwardly from hydraulic breaker 28 and it has a Y-axis with a wedge-platen or disc 34 on its bottom end. Platen 34 would be driven downwardly in a reciprocating motion approximately 4 times per second to tamp the aggregate to its proper density or modulus.

Figure 3:
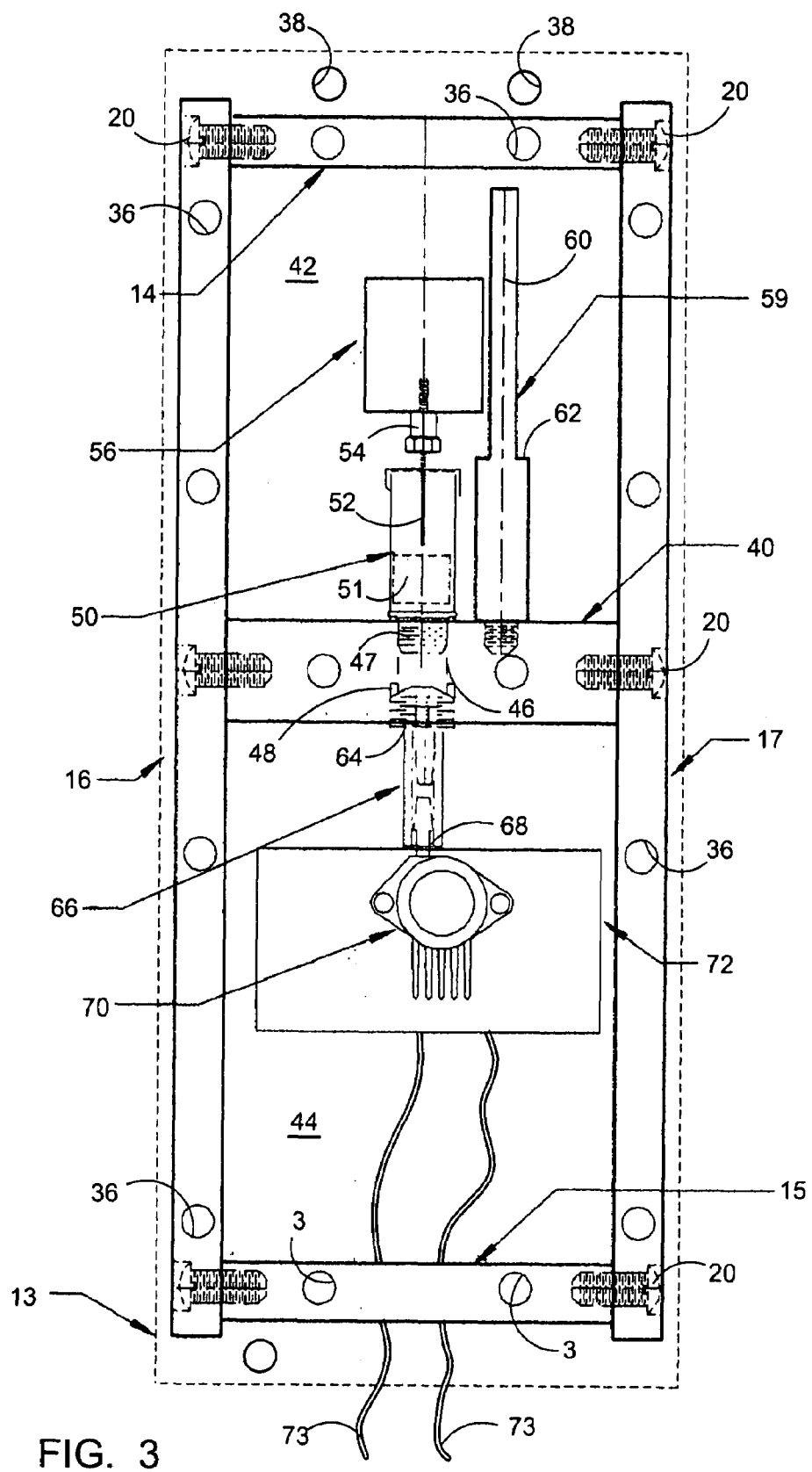
FIG. 3 is a schematic front elevation view of the displacement instrument with the front cover plate removed.

FIG. 3 is a schematic front elevation view of the displacement instrument 10 with front cover 12 removed. Threaded bolt apertures 36 show where bolts 20 have been removed in taking off front cover 12. Threaded bolt apertures 38 in rear plate wall 13 are used for attaching the housing or casing to side plate 29 of the hydraulic breaker 28. A center support plate 40 extends fully between front plate wall 12 and rear plate wall 13 to form an upper chamber 42 and a lower chamber 44. Center support plate 40 has a centrally located bore hole 46 that passes entirely through its thickness. Bore hole 46 has internal threads 47 at its top end and internal threads 48 at its bottom end.

An air cylinder 50 has a tubular bottom end with external threads that are screwed into internal threads 47 of bore hole 46. A piston 51 having a piston rod 52 is reciprocally movable upwardly and downwardly in air cylinder 50. A connector 54 is threaded on the top end of rod 52. The top end of connector 54 is threaded into a cylindrical mass 56. Mass 56 is made of metal material and in this embodiment it is made of brass. Three vertically oriented guide pins/or rods 59 are equally spaced around mass 56 and have their bottom ends screwed into threaded bores in the top of center support plate 40. Only one of the guide pin/rods 59 is shown for clarity. Each guide pin/rod 59 has a neck portion 60 upon which the outer periphery of mass 56 slides upwardly and downwardly. Shoulder 62 provides a bottom limit stop for mass 56 as it travels downwardly.

A tubular connector plug 64 has its top end screwed into the internal threads 48 of bore hole 46. An air tube 66 is clamped onto the bottom end of connector plug 64. Air tube 66 is made of flexible material such as medical tubing. The bottom end of air tube 66 is clamped onto the top end of tubular air inlet 68 of air pressure transducer 70. There is therefore an open air passage way or air chamber between the bottom end of air cylinder 50 all of the way down to air inlet port 68 of air pressure transducer 70. When piston 51 travels downwardly it will compress the air in the air chamber and create an air pressure force into the top end of air pressure transducer 70. Air pressure transducer 70 is mounted on the printed circuit board 72 and floats freely within lower chamber 44 without being restricted in any lateral direction. Center support plate 40 serves as an umbilical and mounting plate for the air cylinder 50 and air tube 66, which is connected to the air pressure transducer 70. Air tube 66 is flexible and serves as a shock mounting for the circuit board 72. Wires 73 extend from transducer circuit board 72 and their purpose will be described later.

The displacement instrument is firmly mounted on hydraulic breaker 28 whose movement along a prescribed Y-axis is to be measured. As the device is moved abruptly downward along the Y-axis, mass 56 initially because of inertia remains in its vertical position until platen 34 strikes the aggregate now being compressed. At this instant the piston is driven downwardly and compresses the air below it within the air chamber producing an electrical signal whose voltage output amplitude is proportional to the pressure within the air chamber. After the platen 34 strikes the aggregate, the piston will automatically return to its initial position because the compressed air that has been pushed into the transducer will automatically push the piston upwardly.

A mass in the hydraulic breaker 28 applies 3000 psi to the shaft 32 of the hydraulic breaker 28. The crane operator pre-loads the shaft by bringing the crane up on its rear end. This pre-loads the hydraulic breaker to 12,000 psi so that when the tamper platen 34 hits the aggregate it has a force of 15,000 psi force driving it into the aggregate. Platen 34 is being driven downwardly 4 times per second. At each hit you get an output voltage from the air pressure transducer. You get a large voltage output to begin with and as it becomes harder to compress the aggregate, you have less output voltage. This output voltage is illustrated in an output signal such as illustrated in FIG. 6. When the output voltage returns to a predetermined lower level, the hydraulic breaker will be automatically shut off since the aggregate has reached its full compression. The displacement instrument is thus making a measurement that gives us an electrical pulse which equates to the amount of force that is applied to the aggregate.

Figure 4:
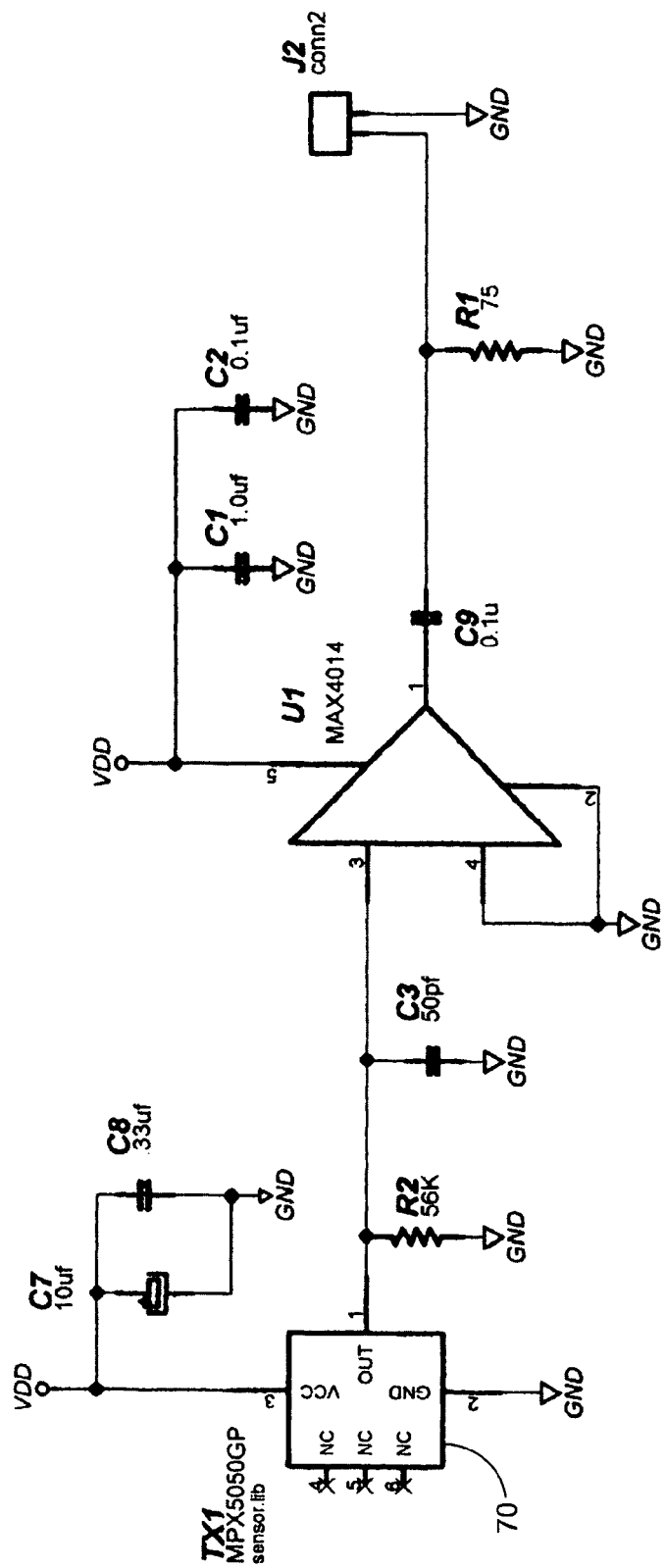
FIG. 4 shows the electrical circuitry for the pressure transducer mounted on the printed circuit board.
Figure 8:
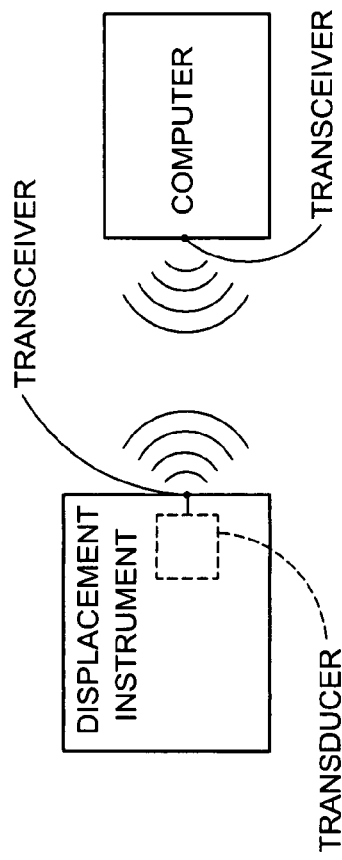
FIG. 8 shows an alternative embodiment block diagram showing a wireless electrical connection between the pressure transducer and a computer.

FIGS. 4 and 5 show the electronic circuitry mounted on circuit boards 72. Pressure transducer 70 has its output voltage applied to R2, C3 and U1. U1 is an operational amplifier which gives you unity out versus unity in. In other words if you put 100 millivolts in, you get 100 millivolts out. Its only function is to transfer the impedance. It has a very high impedance output of 56K. This means that it has a very low current input. The output has 75 ohms so there is a high output current. R2 and C3 perform signal shaping, noise reduction and some impedance adjustment to the output of pressure transducer 70 to the input of U1. U1 is a linear gain operational amplifier with high input impedance and low output impedance where voltage in is equal to voltage out. As an example, 0.5v having high impedance in equals 0.5 impedance Z out. C9 is a coupling capacitor and eliminates the 0.5 output offset of U1. R1 provides a low impedance load to drive a twisted pair low impedance line. C1, C2, C4, CS, C6, C7 and C8 provide noise reduction and spike suppression. VDD is the supply voltage in FIG. 4. That is the supply that comes from the voltage regulator U2 in FIG. 5. This is a 5-volt supply. The VCC is the input voltage in FIG. 5. It comes in at 12 volts and goes out at 5 volts from U2. J1 is simply a connector to the printed circuit board. The J2 connector is the electrical signal output to the computer.

Pressure transducer 70 is pressured by mass 56 falling and this is the output that goes into one side of the operation output amplifier U1. This is a linear function device.

FIG. 6 represents voltage impulse signal that is produced each time platen 34 strikes the aggregate. The voltage amplitude decreases each time because the mass is moving less distance each successive strike so there is less compressed air and there is less voltage output. The system is working to until the voltage output gets down to about 220 mv before it turns off. The original output is clamped at 1.2 volts. About 220 millivolts gives a modulus of 350-400. When it is desired to obtain a certain modulus, the voltage used can be set up accordingly.

Penetration is checked on each hole and it is measured after each new 12-18 inches of aggregate is put into the hole. If a 300 modulus is desired, the instrument can be set up to stop when the 300 modulus is reached.

Presently in the prior art there is no available method or system to determine the modulus of compressed of the aggregate. No one knows what the impaction reading might be. What is acceptable procedure now is load testing after the building structure has been built. There is presently no way of knowing what the modulus is at the bottom of a twenty foot hole or thirty foot hole or fifteen foot hole. Presently they make broad assumptions and hit the aggregate for so many seconds and that is the end of the process. Presently existing systems cannot determine what the modulus is or what the load test will average out to more than about three to four feet below the surface of the ground. As the platen compacts the aggregate, it also spreads out so that if you look at it from the side it appears like a pile of donuts stacked on top of each other with a solid core. The compacted aggregate is locked into the side soil.

Figure 7:
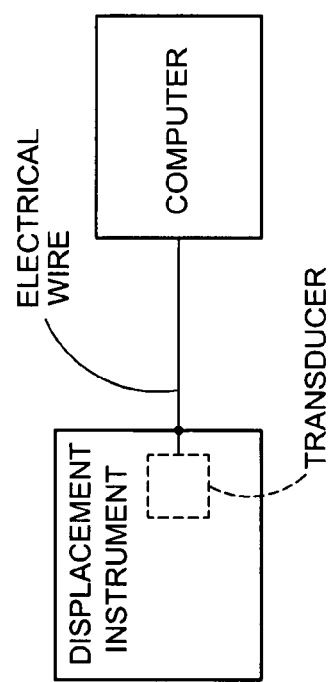
FIG. 7 is a block diagram showing the pressure transducer connected to a computer by electrical wires.

The pulses coming out of connector J2 are supplied to a computer where it is processed via proprietary software. The computer displays the desired information and prints a copy of the output signal from U1, which indicates the modulus of the material. U2 is a precision voltage regulator with 5v output and will accept an input of 8 volts to 35 volts. FIG. 7 is a block diagram showing the displacement instrument connected by an electrical wire to a computer. FIG. 10 is a wireless embodiment.

Although this invention has been described in connection with specific forms and embodiments thereof, it will be appreciated that various modifications other than those discussed above may be resorted to without departing from the spirit or scope of the invention. For example, equivalent elements may be substituted for those specifically shown and described, certain features may be used independently of other features, and the number and configuration of various components described above may be altered, all without departing from the spirit or scope of the invention as defined in the appended claims.

The invention claimed is:

1. A displacement instrument for determining a modulus of a material, comprising:

a vertically oriented casing having an interior therein; a horizontally oriented support member in said interior of said casing divides said casing into an upper chamber and a lower chamber; said support member having a top surface and a bottom surface; a bore hole extends vertically down through said support member from said top surface to said bottom surface;

a vertically oriented air cylinder having a top end, a bottom end, and a piston in said air cylinder that can travel reciprocally up and down in said air cylinder; said bottom end of said air cylinder having an air outlet port; said bottom end of said air cylinder being connected to said top surface of said support member with said air outlet port being in communication with said bore hole of said support member; a vertically oriented piston rod has a bottom end connected to said top end of said piston; said piston rod having a top end that extends upwardly through said top end of said air cylinder;

a mass is located in said upper chamber and it has a bottom surface;

a first connector for connecting said top end of said piston rod to said bottom surface of said mass;

an air pressure transducer located in said lower chamber; said air pressure transducer having an air inlet port;

a second connector for connecting said air inlet port of said air pressure transducer to said bottom end of said bore hole in said support member thereby forming an air pressure chamber that extends from said bottom end of said air cylinder into said air pressure transducer;

an electrical circuit connected to said air pressure transducer capable of creating an electrical voltage output signal in response to said piston in said air cylinder being driven downwardly by said mass that compresses the air in said air pressure chamber; and a third connector capable of delivering the output signal to a computer adapted to determine the modulus of the material.

2. A displacement instrument as recited in claim 1 wherein said casing is rigidly connected to a side plate on the hydraulic breaker on the boom of a crane.

3. A displacement instrument as recited in claim 1 wherein said electrical voltage output signal is connected by an electrical wire to the computer.

4. A displacement instrument as recited in claim 1 wherein said electrical voltage output signal is connected by a wireless system to the computer.

5. A displacement instrument as recited in claim 1 wherein said casing is made of a top plate member, a bottom plate member, a rear plate member, a left side plate member, a right side plate member and a front cover plate member.

6. A displacement instrument as recited in claim 5 wherein said plate members are all made of metal.

7. A displacement instrument as recited in claim 1 further comprising a guide for controlling the alignment of said mass as it reciprocally travels upwardly and downwardly.

8. A displacement instrument as recited in claim 7 wherein said guide comprises a plurality of vertically oriented guide pins surrounding said mass and having their bottom ends secured to said top surface of said support member.

* * * * *